(12) United States Patent
Williams

(10) Patent No.: US 11,877,833 B2
(45) Date of Patent: *Jan. 23, 2024

(54) SYSTEMS AND METHODS FOR MONITORING BLOOD PRESSURE WITH A POWERED LINEAR DRIVE

(71) Applicant: Covidien LP, Mansfield, MA (US)

(72) Inventor: Justin Williams, Southbury, CT (US)

(73) Assignee: Covidien LP, Mansfield, MA (US)

(*) Notice: Subject to any disclaimer, the term of this patent is extended or adjusted under 35 U.S.C. 154(b) by 605 days.

This patent is subject to a terminal disclaimer.

(21) Appl. No.: 16/890,259

(22) Filed: Jun. 2, 2020

(65) Prior Publication Data

US 2021/0022630 A1 Jan. 28, 2021

Related U.S. Application Data

(60) Provisional application No. 62/878,816, filed on Jul. 26, 2019.

(51) Int. Cl.
*A61B 5/022* (2006.01)
*A61B 5/00* (2006.01)

(52) U.S. Cl.
CPC ........ *A61B 5/02233* (2013.01); *A61B 5/0004* (2013.01); *A61B 5/742* (2013.01); *A61B 2562/0238* (2013.01)

(58) Field of Classification Search
None
See application file for complete search history.

(56) References Cited

U.S. PATENT DOCUMENTS

| 4,109,647 A | 8/1978 | Stern et al. |
| 4,233,743 A * | 11/1980 | Flick ................ G01B 3/20 600/587 |
| 4,862,894 A | 9/1989 | Fujii |

(Continued)

FOREIGN PATENT DOCUMENTS

| EP | 1974676 A1 | 10/2008 |
| EP | 2573190 A1 | 3/2013 |

(Continued)

OTHER PUBLICATIONS

European Search Report dated Oct. 8, 2020, issued in corresponding EP Appln. No. 20187314, 9 pages.

(Continued)

*Primary Examiner* — Etsub D Berhanu
*Assistant Examiner* — Samuel C Kim
(74) *Attorney, Agent, or Firm* — Carter, DeLuca & Farrell LLP

(57) ABSTRACT

A tissue property sensing system includes a sensing assembly that is movable along a drive screw and includes an outer shaft, an anvil, a center drive, a piston, and a tension spring. The piston includes a distal arm having a distal portion and a head that extends from the distal portion. The piston is movable within the outer shaft to move the head in relation to the anvil between an open configuration and a closed configuration, wherein in the closed configuration, the head of the piston and the anvil are positioned to clamp and occlude flow of blood within tissue. The tension spring is coupled to the center drive and to the piston to urge the piston towards the center drive and to urge the head of the piston towards the anvil.

17 Claims, 9 Drawing Sheets

(56) References Cited

U.S. PATENT DOCUMENTS

| | | | |
|---|---|---|---|
| 5,395,033 | A | 3/1995 | Byrne et al. |
| 5,518,164 | A | 5/1996 | Hooven |
| 5,722,419 | A | 3/1998 | Semmlow et al. |
| 5,769,791 | A | 6/1998 | Benaron et al. |
| 7,172,104 | B2 | 2/2007 | Scirica et al. |
| 7,223,279 | B2 | 5/2007 | Burbank et al. |
| 7,229,465 | B2 | 6/2007 | Burbank et al. |
| 7,618,376 | B2 | 11/2009 | Kimball |
| 8,002,795 | B2 | 8/2011 | Beetel |
| 8,073,518 | B2 | 12/2011 | Chin |
| 8,118,206 | B2 | 2/2012 | Zand et al. |
| 8,157,145 | B2 | 4/2012 | Shelton, IV et al. |
| 8,808,311 | B2 | 8/2014 | Heinrich et al. |
| 9,204,830 | B2 | 12/2015 | Zand et al. |
| 11,547,439 | B2 * | 1/2023 | Williams ............ A61B 17/2909 |
| 2003/0120306 | A1 | 6/2003 | Burbank et al. |
| 2003/0212435 | A1 * | 11/2003 | Gold ................ A61B 17/122 606/206 |
| 2004/0127800 | A1 | 7/2004 | Kimball et al. |
| 2005/0101974 | A1 | 5/2005 | Burbank et al. |
| 2005/0131390 | A1 | 6/2005 | Heinrich et al. |
| 2006/0235314 | A1 | 10/2006 | Migliuolo et al. |
| 2009/0234248 | A1 | 9/2009 | Zand et al. |
| 2010/0185220 | A1 * | 7/2010 | Naghavi ............ A61B 5/14546 600/301 |
| 2011/0144640 | A1 | 6/2011 | Heinrich et al. |
| 2012/0116185 | A1 | 5/2012 | Zand et al. |
| 2014/0107697 | A1 | 4/2014 | Patani et al. |
| 2014/0135604 | A1 | 5/2014 | Cuesta Valentin et al. |
| 2014/0148751 | A1 | 5/2014 | Kassab et al. |
| 2014/0288386 | A1 | 9/2014 | Zand et al. |
| 2015/0066000 | A1 | 3/2015 | An et al. |
| 2016/0066914 | A1 * | 3/2016 | Baber .................. G06F 1/30 227/176.1 |
| 2016/0118201 | A1 | 4/2016 | Nicholas et al. |
| 2017/0095251 | A1 * | 4/2017 | Thompson ......... A61B 17/3468 |
| 2019/0175215 | A1 | 6/2019 | Williams |
| 2019/0175216 | A1 | 6/2019 | Williams |

FOREIGN PATENT DOCUMENTS

| | | |
|---|---|---|
| EP | 2742873 A1 | 6/2014 |
| TW | 201409026 A | 3/2014 |
| WO | 03101277 A2 | 12/2003 |
| WO | 2006113394 A2 | 10/2006 |
| WO | 2007008057 A1 | 1/2007 |
| WO | 2008085025 A1 | 7/2008 |

OTHER PUBLICATIONS

European Office Action dated Jan. 31, 2023, issued in corresponding EP Appln. No. 20187314, 5 pages.

* cited by examiner

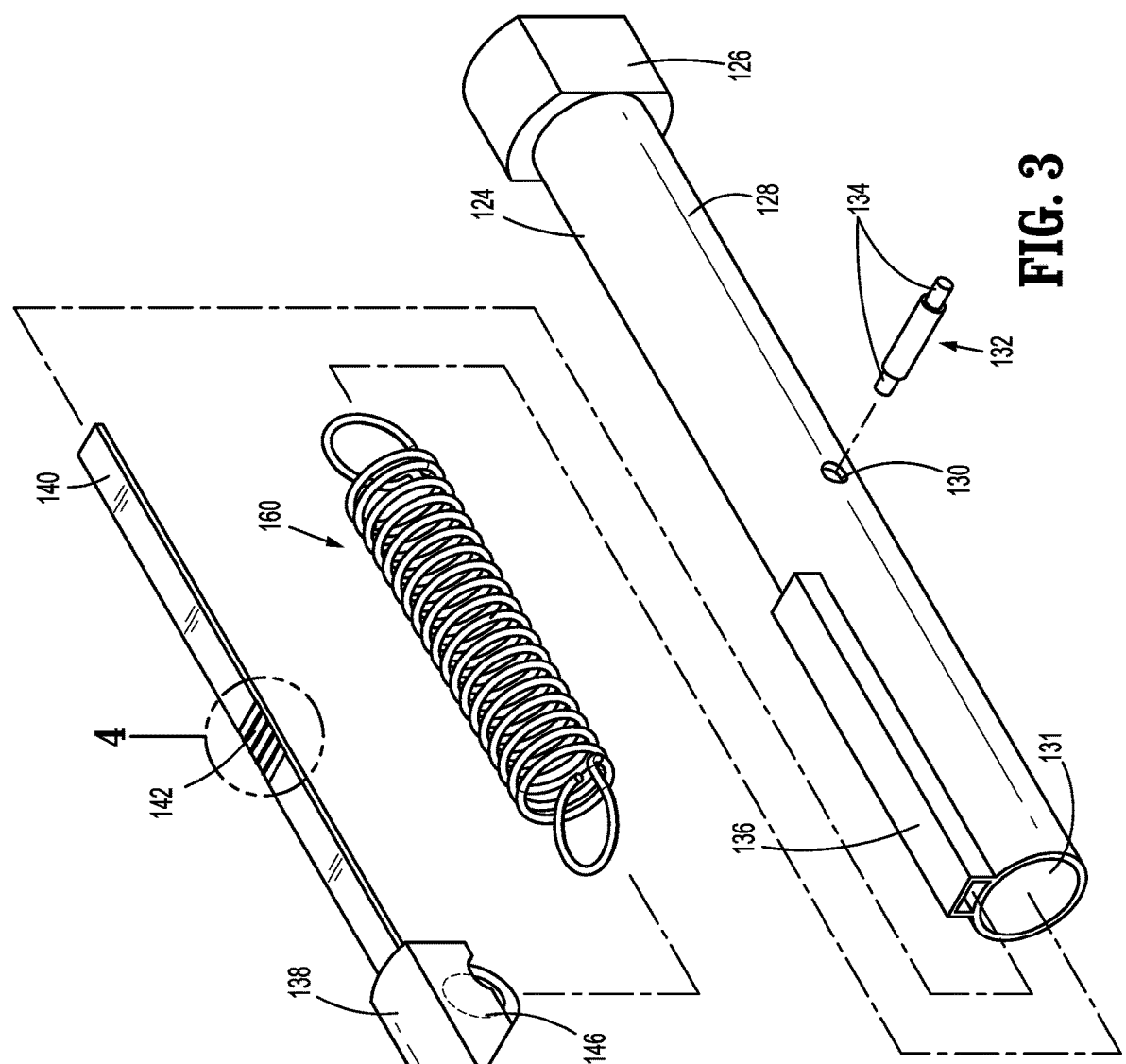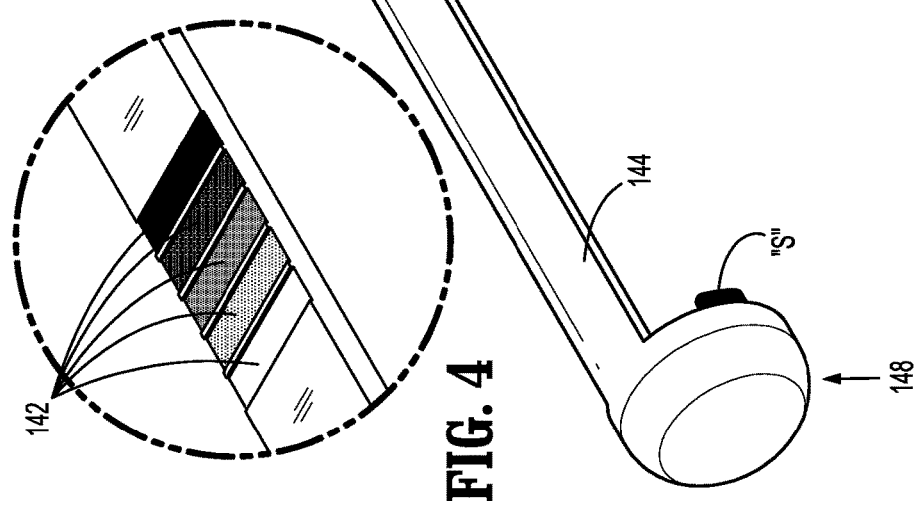

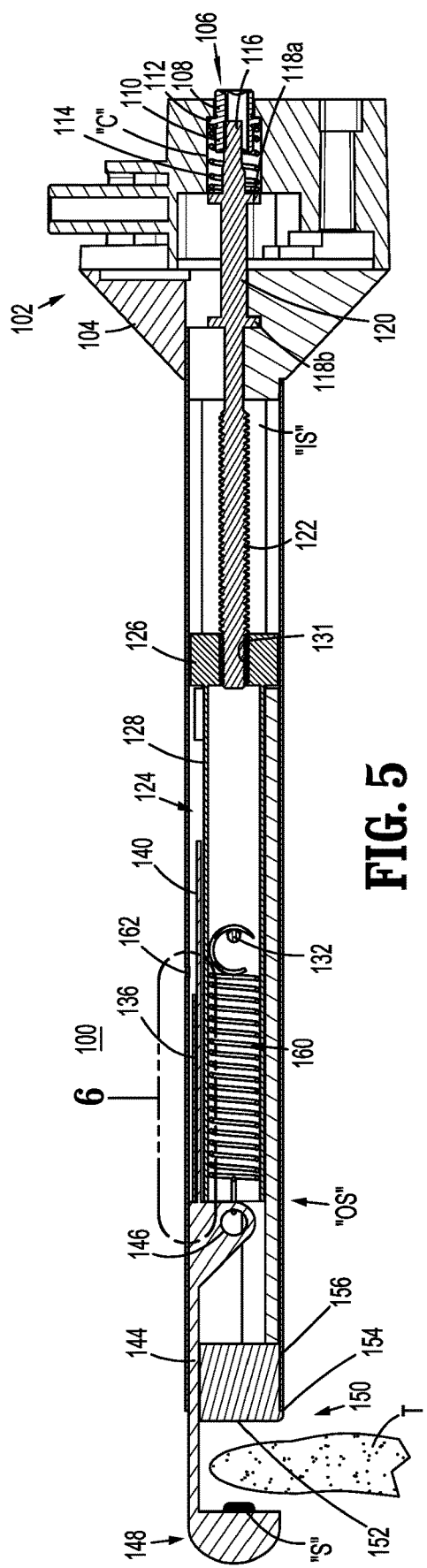
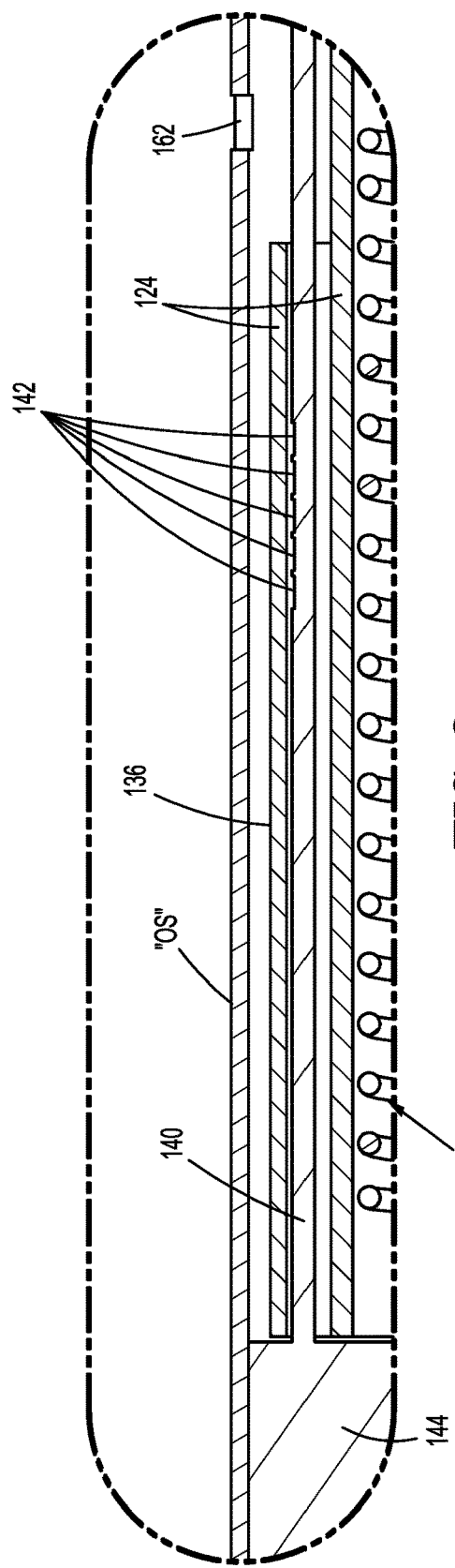

SYSTEMS AND METHODS FOR MONITORING BLOOD PRESSURE WITH A POWERED LINEAR DRIVE

CROSS-REFERENCE TO RELATED APPLICATIONS

This application claims the benefit of and priority to U.S. Provisional Patent Application Ser. No. 62/878,816 filed Jul. 26, 2019, the entire disclosure of which is incorporated by reference herein.

FIELD

The present disclosure is directed to systems and methods for measuring tissue properties and, more particularly, to systems and methods for occluding blood flow in target tissue during minimally-invasive surgeries to measure tissue properties.

BACKGROUND

During surgical procedures medical professionals or clinicians may find it desirable to determine one or more tissue properties prior to acting upon the tissue. For example, during colorectal surgeries which require anastomosis, the clinician visually inspects the tissue of the colon to be resected. Typically, during inspection, the clinician visually observes the colon and determines which portion or portions of the colon are diseased. The clinician then identifies which diseased portions of the colon will be removed. Observation may be performed via one or more imaging devices positioned within the colon or proximate to the colon. Various other surgical procedures require similar visual inspection of tissue to determine which portions of tissue are to be removed.

Depending on the procedure and the tissue being examined, the clinician may not be able to identify all areas of concern due to the limited visibility of the clinician. For example, referring again to anastomotic procedures, the colon may include an abnormal growth which may not be easily visualized from an inspection of the exterior of the colon. As such, the clinician may need to inspect the interior of the tissue to be resected as well. Inspection of the interior of the colon may require additional clinicians and/or imaging or visualization devices, e.g., endoscopes, to assist in imaging the interior of the colon. Care must be taken when aligning the interior and exterior views during the imaging process.

As such, improved devices and methods for evaluating tissue properties during a surgical procedure are desirable.

SUMMARY

One aspect of the present disclosure is directed to a tissue property sensing system including an adapter assembly having a drive interface, a drive screw, and a sensing assembly. The drive screw is coupled to the drive interface of the adapter assembly and extends from the adapter assembly. The sensing assembly is movable along the drive screw and includes an outer shaft, an anvil, a center drive, a piston, and a tension spring. The anvil is supported on a distal portion of the outer shaft. The center drive is movable within the outer shaft and defines a longitudinal bore. The piston includes a distal arm having a distal portion, and a head that extends from the distal portion of the distal arm. The piston is movable within the outer shaft to move the head in relation to the anvil between an open configuration and a closed configuration, wherein in the closed configuration, the head of the piston and the anvil are positioned to clamp and occlude flow of blood within tissue. The tension spring is coupled to the center drive and to the piston to urge the piston towards the center drive and to urge the head of the piston towards the anvil.

In embodiments, the head of the piston supports at least one sensor.

In some embodiments, the piston includes a proximal arm and the center drive includes a housing, wherein the proximal arm is received within the housing to prevent rotatable movement of the piston in relation to the center drive.

In certain embodiments, the center drive includes a threaded opening, and a portion of the drive screw is received within the threaded opening such that rotation of the drive screw in relation to the center drive causes longitudinal movement of the center drive within the outer shaft.

In embodiments, rotation of the drive screw in a first direction causes the center drive to move distally in relation to the adapter assembly and rotation of the drive screw in a second direction causes the center drive to move proximally in relation to the adapter assembly.

In some embodiments, in the closed configuration, the sensing assembly applies a predetermined range of forces to tissue disposed within the sensing assembly.

In certain embodiments, the outer shaft defines a window and the proximal arm of the piston supports a plurality of indicators, wherein one or more of the plurality indicators is visible through the window in the closed configuration to indicate a thickness of the tissue positioned between the head of the piston and the anvil.

In embodiments, a sensor is disposed on one of the head of the piston or the anvil.

In some embodiments, the center drive supports a fixation pin that is disposed within the longitudinal bore and the tension spring is coupled to the fixation pin.

Another aspect of the present disclosure is directed to a method of sensing blood pressure within a tissue property sensing device, wherein the method includes positioning tissue between a head of a piston and an anvil which are coupled together via a spring having a known spring constant; occluding a flow of blood within the tissue by moving the head of the piston and the anvil of the tissue property sensing device to a closed configuration and increasing tension in the tension spring; moving the head of the piston away from the anvil to reduce pressure exerted on the target tissue to allow the blood to begin to flow again within the tissue; and calculating a systolic blood pressure of a patient taken at the tissue when the blood within the target tissue begins to flow again.

In embodiments, after determining the systolic blood pressure of the patient, the method includes moving the head of the piston further away from the anvil so that the flow of blood within the tissue is not occluded; and calculating a diastolic blood pressure of the patient taken at the tissue when it is determined that flow of blood within the target tissue is not occluded.

In some embodiments, determining the systolic blood pressure includes determining a position of the head of the piston relative to a fixed component of the tissue property sensing device when the blood begins to flow again within the tissue, calculating a length of the spring based on the determined position; and based on the length of the spring, calculating a force exerted by the spring on the tissue.

In embodiments, determining the diastolic blood pressure includes determining a position of the head of the piston relative to a fixed component of the tissue property sensing device in response to determining that blood flow is no longer occluded in the tissue, calculating a length of the spring based on the determined position, and based on the length of the spring, calculating a force exerted by the spring on the tissue.

BRIEF DESCRIPTION OF THE DRAWINGS

Various embodiments of the disclosed systems and methods are described herein below with reference to the drawings, wherein:

FIG. 3 is an enlarged view of the indicated area of detail of FIG. 1;

FIG. 4 is an enlarged view of the indicated area of detail shown in FIG. 3;

FIG. 5 is a cross-sectional view taken along section line 5-5 of the tissue property sensing device of FIG. 1 in an open configuration;

FIG. 6 is an enlarged view of the indicated area of detail of FIG. 5;

DETAILED DESCRIPTION

Figure 1:
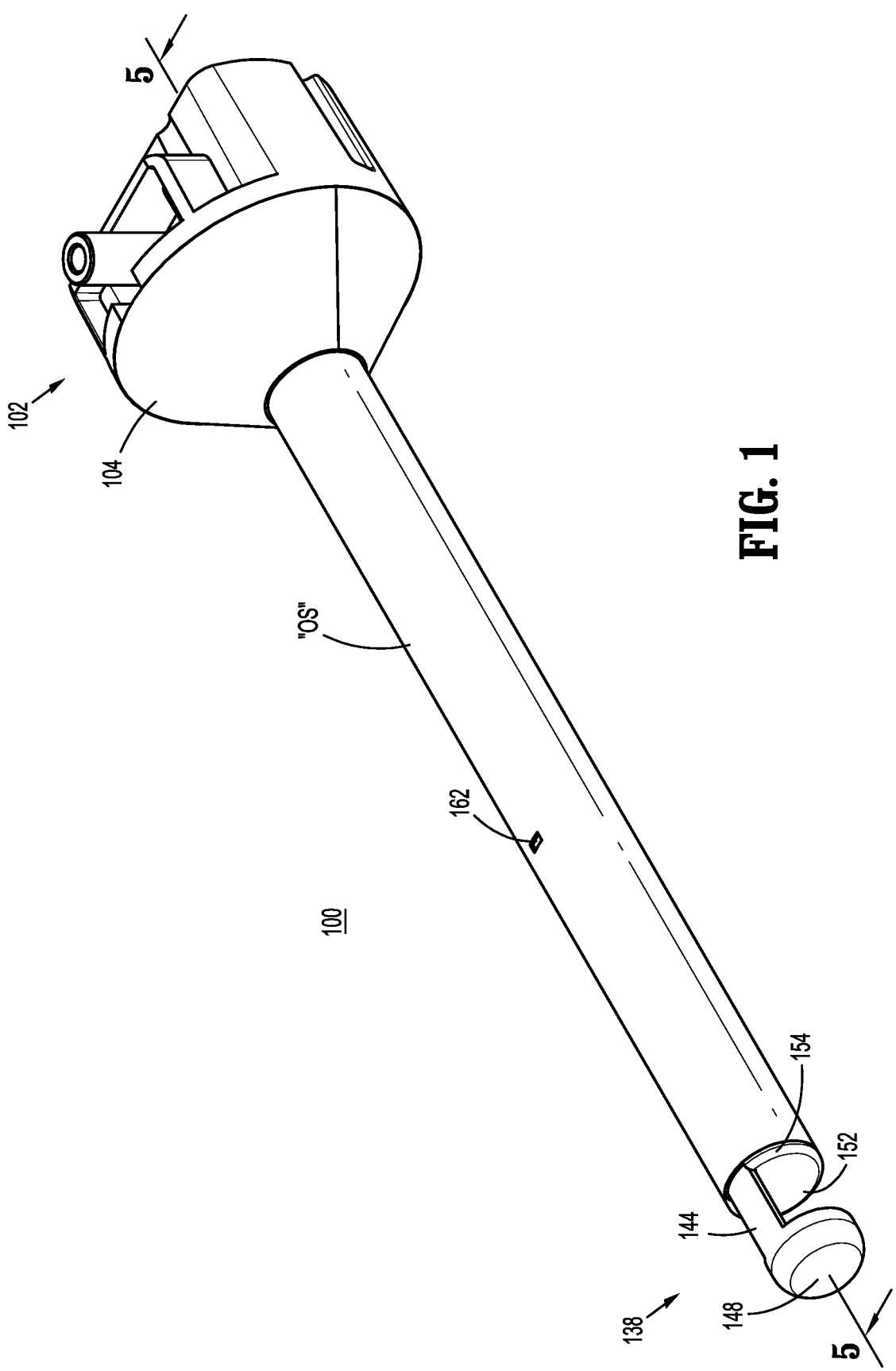
FIG. 1 is a side perspective view of a tissue property sensing device with a sensing assembly in an open configuration, according to exemplary embodiments of the present disclosure.

The disclosed tissue property sensing device will now be described in detail with reference to the drawings. It will be understood that like reference numerals may designate identical or corresponding elements in each of the several views. As used herein, the term "proximal" generally refers to that portion of the described element or feature which is closer to a clinician, while the term "distal" generally refers to that portion of the described element or feature which is farther from the clinician; the term "clinician" generally refers to medical personnel including doctors, surgeons, nurses, support personal, and the like; and directional terms such as front, rear, upper, lower, top, bottom, distal, proximal, and similar terms are used to assist in understanding the description and are not intended to limit the present disclosure.

Referring now to FIGS. 1-4, an embodiment of a tissue property sensing device is designated generally as tissue property sensing device 100. The tissue property sensing device 100 includes an adapter assembly 102 that is configured to couple to remote devices such as, for example, a handheld device 200 (FIG. 11) or a robotic surgical system (not shown). For purposes of clarity, reference will be made generally to connection and operation of the tissue property sensing device 100 to the handheld device 200 (FIG. 11), though it will be understood that connection and operation may similarly be made to a robotic surgical system. Examples of such systems may be found by reference to U.S. Patent Application Publication No. 2015/0157320 to Zergiebel et al., filed on Nov. 21, 2014, now U.S. Pat. No. 9,918,713, entitled "ADAPTER ASSEMBLY FOR INTERCONNECTING ELECTROMECHANICAL SURGICAL DEVICES AND SURGICAL LOADING UNITS, AND SURGICAL SYSTEMS THEREOF," U.S. Patent Application Publication No. 2016/0310134 to Contini et al., filed on Apr. 12, 2016, entitled "HANDHELD ELECTROMECHANICAL SURGICAL SYSTEM," and U.S. Pat. No. 8,828,023, the entire contents of each of which are hereby incorporated by reference in their entirety. Although the handheld device 200 (FIG. 11) is illustrated as an electrically powered device, it is envisioned that manually powered handheld devices may also be provided to drive the tissue property sensing device 100.

Figure 2:
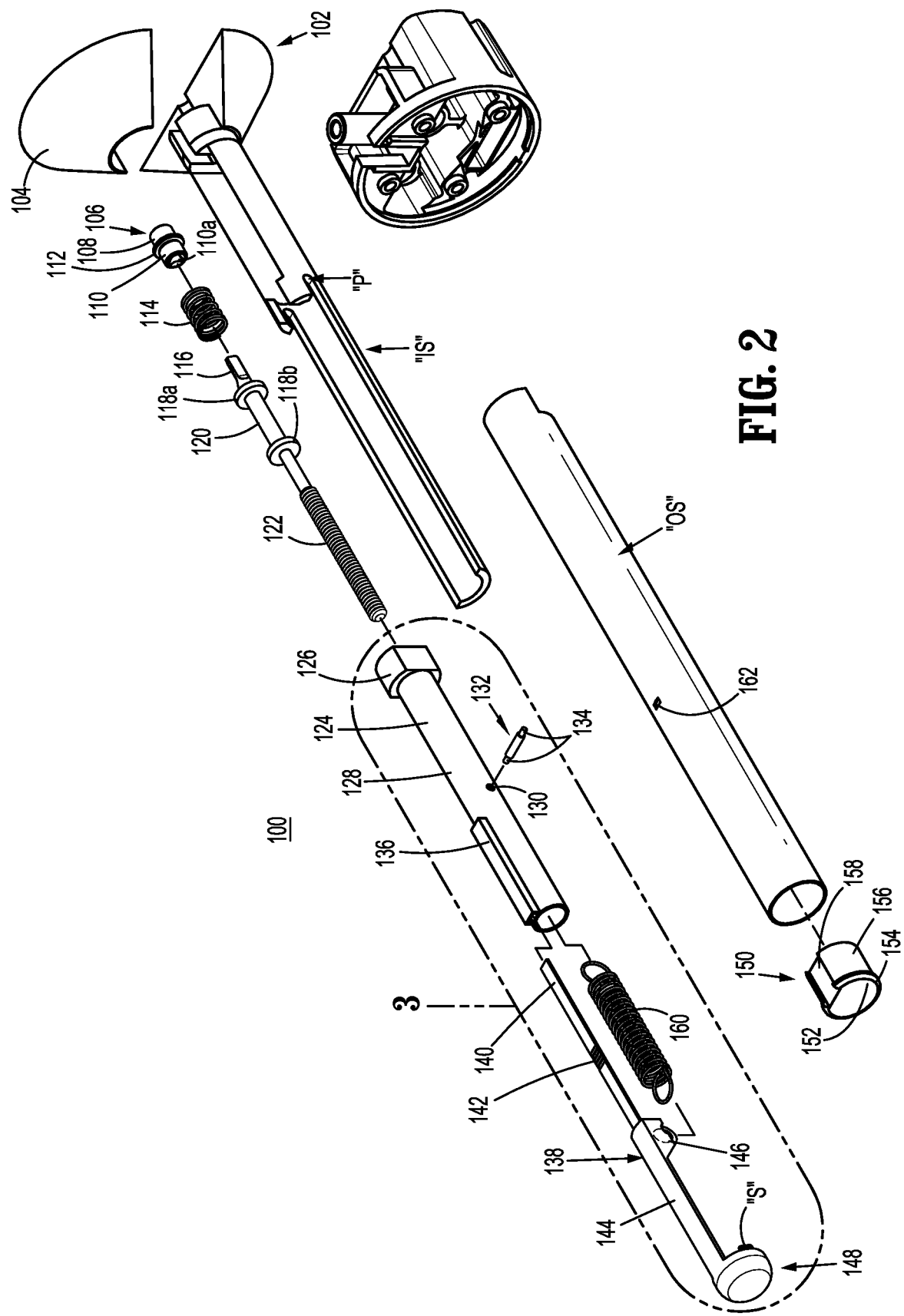
FIG. 2 is a side perspective view of the tissue property sensing device of FIG. 1 with parts separated.
Figure 11:
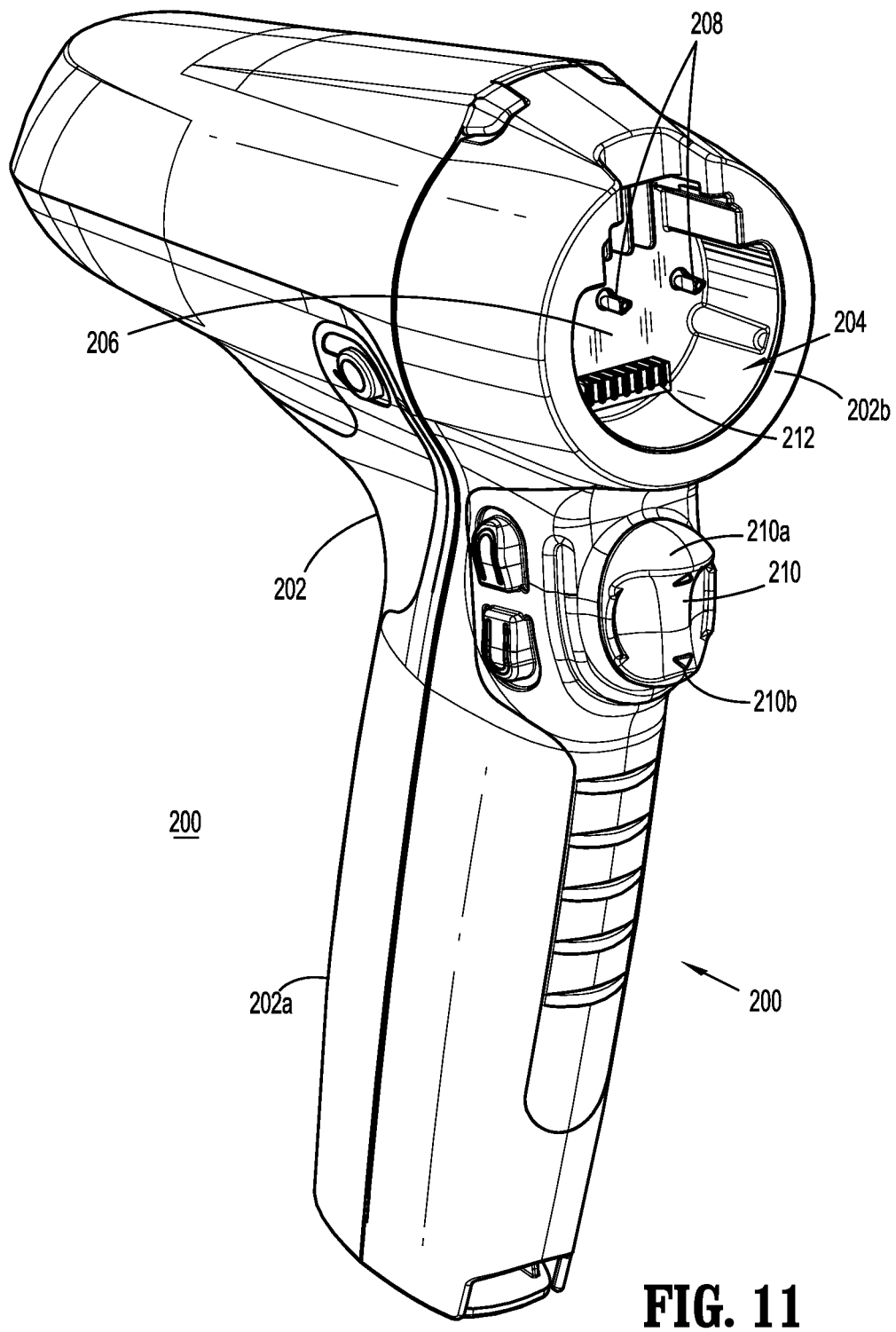
FIG. 11 is a perspective view of a handle assembly for connection with the tissue property sensing device of FIG. 1.

Referring to FIGS. 2 and 5, the adapter assembly 102 includes an adapter interface having one or more proximal connector sleeves 108 (FIG. 5) configured to receive one or more drive screws 208 (FIG. 11) that extend from the handheld device 200 (see FIG. 11). In response to engagement of a motor (e.g., a motor of the handheld device 200 or a robotic surgical system, not explicitly shown), the drive screw 208 rotates the proximal connector sleeve 108 either clockwise or counter-clockwise. The proximal connector sleeve 108 may be operably coupled to a drive interface 106, and it will be understood that in embodiments (as shown in FIG. 2) both the proximal connector sleeve 108 and the drive interface 106 may be integrally formed and/or may be the same component. For a detailed description of the operation and engagement of an adapter (e.g., adapter assembly 102) by a handheld device 200, reference may be made to U.S. Provisional Patent Application No. 62/597,595, entitled "SURGICAL INSTRUMENTS INCLUDING DEVICES FOR SENSING TISSUE PROPERTIES AND METHODS THEREOF," by Williams, filed on Dec. 12, 2017, the entire contents of which are hereby incorporated by reference in their entirety.

The drive interface 106 includes a flange 112 extending around a periphery of the drive interface 106. The flange 112 is configured to engage a proximal portion of a compression spring 114, and receive longitudinal forces exerted from the compression spring 114 to urge the drive interface 106 proximally in a cavity "C" (FIG. 5) of the housing 104 of the adapter assembly 102. The drive interface 106 further includes a distal connector sleeve 110 that defines a corresponding recess extending inwardly from a distal portion of the drive interface 106 proximally. The proximal connector sleeve 108 and the distal connector sleeve 110 are configured to receive the drive screw 208 (FIG. 11) and a drive head 116, respectively. In embodiments, when rotatably coupled to the one or more drive screws 208 (FIG. 11), the drive interface 106 may be engaged or disengaged by advancing the one or more drive screws 208 of the handheld device 200 distal or proximal relative to the proximal connector sleeve 108. Such distal and proximal advancement of the one or more drive screws 208 either causes the compression spring 114 to compress or decompress, in turn causing a proximal portion of the drive head 116 to enter or exit the distal connector sleeve 110 of the drive interface

106. The distal portion of the drive screw 208 has a configuration (e.g., a flat head, a Phillips head, a Torx head, etc.) that corresponds to the configuration of the recess defined by the proximal connector sleeve 108. Similarly, the proximal portion of the drive head 116 has a configuration that corresponds to a recess 110a defined by the proximal connector sleeve 108. The drive head 116 extends distally to form a drive screw shaft 120. In embodiments, the drive screw shaft 120 has a proximal flange 118a and a distal flange 118b that are spaced from each other and extend about the drive screw shaft 120. The proximal flange 118a may be configured to be received in a corresponding channel defined by the housing 104 of the adapter (not explicitly shown), and the distal flange 118b may be disposed about the drive screw shaft 120 and configured to be received in a separate corresponding channel (see FIG. 5) of the housing 104 of the adapter assembly 102 to longitudinally fix the drive screw shaft 120 in relation to the housing 104. The drive screw shaft 120 further includes threads 122 disposed about a distal portion thereof. The threads 122 are configured to rotatably engage corresponding threading defined within a threaded opening of the center drive 124 to cause the center drive 124 to move either proximally or distally when rotated in a first or second direction, respectively. It is contemplated that the drive screw shaft 120 may be formed of any desired metal, plastic, composite, alloy, etc., and in embodiments, may be made of lead.

Referring to FIGS. 3 and 4, the center drive 124 includes a base 126 and a drive housing 128 that extends distal from the base 126. The base 126 and drive housing 128 define a through bore "B". The through bore "B" is defined by an inner surface 131 that includes a threaded portion 127 that is configured to be rotatably engaged by the threads 122 of the drive screw shaft 120. In embodiments, the threaded portion 127 of the center drive 124 (FIG. 6) may extend along any portion or portions between the proximal and distal portions of the center drive 124. The drive housing 128 defines a pair of apertures 130 (FIG. 2) configured to receive a portion of a fixation pin 132. Specifically, the fixation pin 132 may include spring-loaded and outward biased fixation members 134 disposed within a housing of the fixation pin 132. The fixation members 134 may be advanced inward relative to the housing of the fixation pin 132 prior to insertion of the fixation pin 132 within the lumen of the drive housing 128. The fixation pin 132 may subsequently be aligned with the pair of apertures 130, thereby allowing the fixation members 134 to be move outward and through the pair of apertures 130 to secure the fixation pin 132 within the center drive 124.

The center drive 124 further includes a piston arm housing 136 configured to receive a portion of a proximal piston arm 140 to maintain the angular position of the piston 138 relative to the center drive 124 (e.g., to prevent rotation of the piston 138 relative to the center drive 124). In embodiments (as shown in FIG. 2), the fixation members 134 of the fixation pin 132 may extend outward and be configured to slide along a pin window "P" (FIG. 2) defined at least in part by an inner shaft "IS", thereby limiting rotational movement of the center drive 124 relative to the inner shaft "IS".

Figure 9:
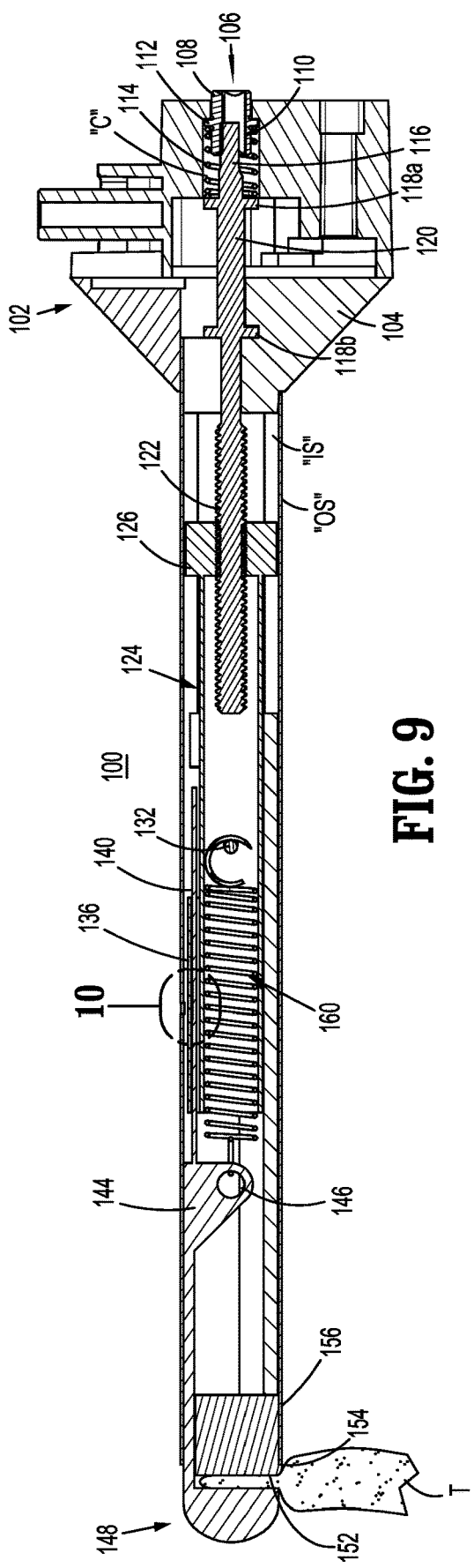
FIG. 9 is a cross-sectional view taken along line 5-5 of the tissue property sensing device of FIG. 1 in a partially-approximated configuration.

With continued reference to FIGS. 1-4, and with particular reference to FIGS. 3 and 4, a sensing assembly includes the center drive 124, a piston 138, and a tension spring 160 that is positioned to exert force on both the center drive 124 and the piston 138 to urge them toward an approximated configuration (FIG. 9.) The piston 138 includes a proximal piston arm 140 and a distal piston arm 144 that extends away from the proximal piston arm 140. The proximal piston arm 140 has a substantially rectangular cross-section, as well as a plurality of indicators 142 disposed along a top portion thereof. The plurality of indicators 142 are configured to be viewed through a window 162 of an outer shaft "OS" (FIG. 2) of the tissue property sensing device 100. The distal piston arm 144 of the piston 138 has a housing which defines an aperture 146 (FIG. 4) located along a proximal portion of the distal piston arm 144. The aperture 146 is configured to receive a distal portion of the tension spring 160. The distal piston arm 144 includes a head 148 that extends inwardly therefrom. In embodiments, the head 148 may be shaped to correspond to the shape of a head 152 of an anvil 150 that is coupled to the outer shaft "OS" of the tissue property sensing device 100. In embodiments, the head 148 of the distal piston arm 144 may support one or more sensors "S" such as, for example, piezoresistive force sensors, optical sensors, impedance sensors, and the like. For a detailed discussion of sensors used in connection with a tissue property sensing device, and sensing systems more generally, reference may be made to U.S. Provisional Patent Application Publication No.: 62/661,821 to Eschbach, entitled "SURGICAL DEVICE INCLUDING SYSTEM FOR SENSING TISSUE PROPERTIES AND METHODS THEREOF," the entire contents of which are hereby incorporated by reference in their entirety.

With continued reference to FIG. 2, the anvil 150 is inserted into an opening defined by a distal portion of the outer shaft "OS" of the tissue property sensing device 100. More particularly, the anvil 150 is fixed along the interior of the outer shaft "OS" by any suitable means such as, without limitation, a friction fit, adhesives, crimps, welds, or other known coupling techniques. The anvil 150 defines the head 152 and includes a flange 154 that extends from a periphery wall 156 of the anvil 150 proximally relative to the head 152. The flange 154 limits proximal movement of the anvil 150 into the outer shaft "OS" of the tissue property sensing device 100 to allow the anvil 150 to receive and compress target tissue thereon, while transferring forces received by the head 152 to the outer shaft "OS". The head 152 of the anvil 150 further includes a channel 158 that is configured to slidably receive the proximal piston arm 140 of the piston 138 therethrough, thereby allowing the proximal piston arm 140 to be inserted into the piston arm housing 136 of the center drive 124 when the anvil 150 is coupled to the outer shaft "OS". The channel 158 is in part formed by an opening in the flange 154 of the anvil 150. It will be understood that, in embodiments, one or more sensors (not explicitly shown) may be disposed in or on the head 152 of the anvil 150, similar to sensors "S" disposed in or on the head 148 of the piston 138.

The drive screw shaft 120, center drive 124, or any other component operably coupled thereto, may be coupled to one or more encoders (not explicitly shown) such as longitudinal or rotational encoders that are disposed along the inner shaft "IS" and/or the outer shaft "OS". The encoders may be in electrical communication (e.g., wired and/or wireless communication) with a controller 300 further described with respect to FIG. 12. The encoders may transmit position data received indicative of either longitudinal or rotational distances traveled by the drive screw shaft 120 and/or the center drive 124. In embodiments, a longitudinal encoder (not explicitly shown) may be coupled to the center drive 124, an interior portion of the outer shaft "OS", and/or various parts of the piston 138 to measure longitudinal motion of the piston 138 relative to the tissue property sensing device 100.

FIGS. 5 and 6 illustrate the tissue property sensing device 100 in an open configuration. To transition the tissue property sensing device 100 to the open configuration, the drive screw shaft 120 is rotated in a first direction (e.g., either clockwise or counter-clockwise), thereby causing the threads 122 of the drive screw shaft 120 to apply a force on the threads of the center drive 124 and cause the center drive 124 to advance along the drive screw shaft 120 within the outer shaft "OS". As the center drive 124 advances, the center drive 124 contacts the distal piston arm 144 and advances the piston 138 such that the head 148 of the piston 138 and the anvil 150 are moved to an open position in spaced relation to each other. Once the piston 138 is moved away from the anvil 150, target tissue (e.g., a portion of the intestines or other tissue located inside the body of a patient) may be positioned between the proximal portion of the head 148 and the anvil 150. As the piston 138 moves within the outer shaft "OS", the indicators 142 are moved out of alignment with the window 162 of the outer shaft "OS".

Figure 7:
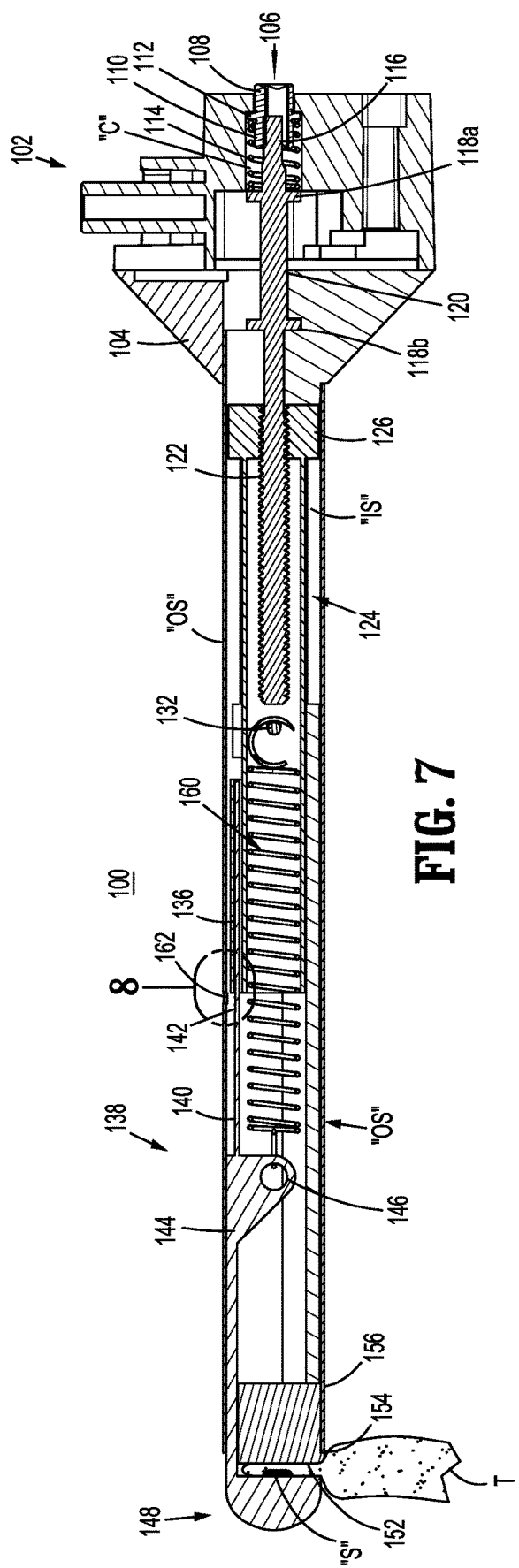
FIG. 7 is a cross-sectional view taken along line 5-5 of the tissue property sensing device of FIG. 1 in an approximated configuration.
Figure 8:
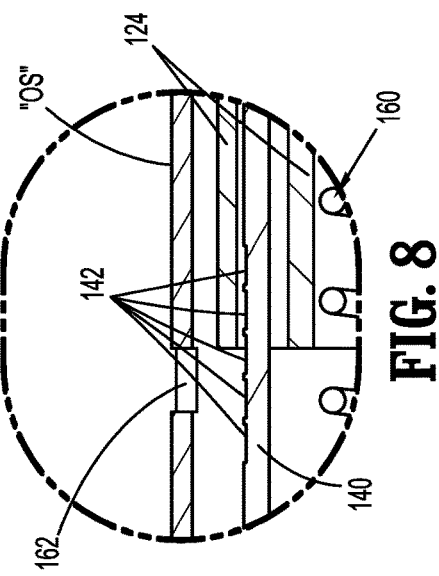
FIG. 8 is an enlarged view of the indicated area of detail of FIG. 7.

FIGS. 7 and 8 illustrate the tissue property sensing device 100 in an approximated configuration. To transition the tissue property sensing device 100 to the approximated configuration the drive screw shaft 120 is rotated in a second direction different from the first direction, causing the threads 122 of the drive screw shaft 120 to apply a force onto the threads of the center drive 124 and cause the center drive 124 to retract within the outer shaft "OS" relative to the drive screw shaft 120. Once retracted, the tension spring 160 exerts a known force proximal to and onto the piston 138. In response to pulling of the center drive 124 on the tension spring 160, the tension spring 160 applies forces proximally and distally to urge the piston 138 and the inner shaft "IS", respectively, toward one another. As shown in FIG. 8, in embodiments the indicators 142 may become visible once the center drive 124 is advanced proximally beyond a predetermined position. Based on the position of the piston 138 relative to the position of the center drive 124, a distance by which the tension spring 160 is expanded may be calculated. The tension exerted by the tension spring 160 may subsequently be calculated based on a known spring constant associated with the tension spring 160 and the expanded distance. In embodiments, the compressive force on tissue compressed between the anvil 150 and the head 148 of the piston 138 may further be determined by dividing the calculated tension in the spring 160 by the area formed by a compressive surface of the anvil 150.

Figure 10:
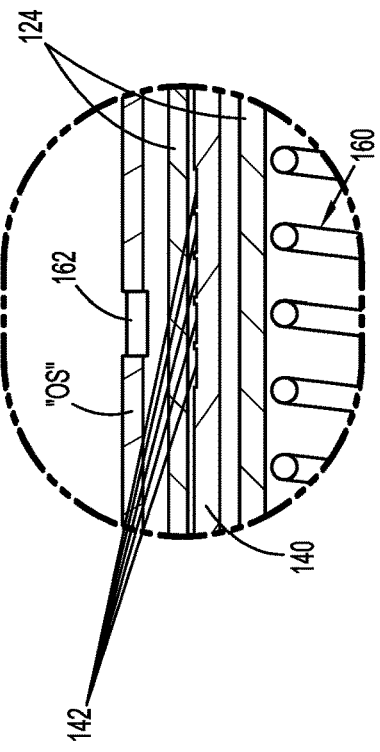
FIG. 10 is an enlarged view of the indicated area of detail of FIG. 9.

Referring now to FIGS. 9 and 10, the tissue property sensing device 100 is shown in an intermediate configuration. To transition the tissue property sensing device 100 to the intermediate configuration, the drive screw shaft 120 is rotated in the first direction, advancing the center drive 124 within the outer shaft "OS". FIG. 11 illustrates a handheld device that is configured to connect to the tissue property sensing device 100 (FIG. 1) and is designated generally as 200. The handheld device 200 includes a housing 202 having a handle portion 202*a*, and a connecting portion 202*b*. The connecting portion 202*b* is configured to selectively couple to the adapter assembly 102. More specifically, the connecting portion 202*b* has a recess 204 which extends proximally inward to a proximal connecting surface 206. The connecting portion 202*b* of handheld device 200 further includes electrical contacts 212 extending distally from the proximal connecting surface 206 and configured to mate with electrical contacts (not explicitly shown) located on the adapter assembly 102. The connecting portion 202*b* of handheld device 200 includes the drive screws 208 which are configured to rotate and mate with the one or more proximal connector sleeves 108 located on the adapter assembly 102 as described above. When the electrical contacts 212 are operably coupled to the housing 104 of the tissue property sensing device 100, the electrical contacts 212 are configured to transmit electrical signals to and from components of the tissue property sensing device 100 including the one or more sensors "S" disposed along the head 148 of the piston 138, and the one or more encoders (not explicitly shown) disposed along the various components of the tissue property sensing device 100. For a detailed description of a handheld device, reference may be made to U.S. Patent Application Publication No. 2016/0310134, filed on Apr. 12, 2016, entitled "HANDHELD ELECTROMECHANICAL SURGICAL SYSTEM", the contents of which are hereby incorporated by reference in their entirety.

Figure 12:
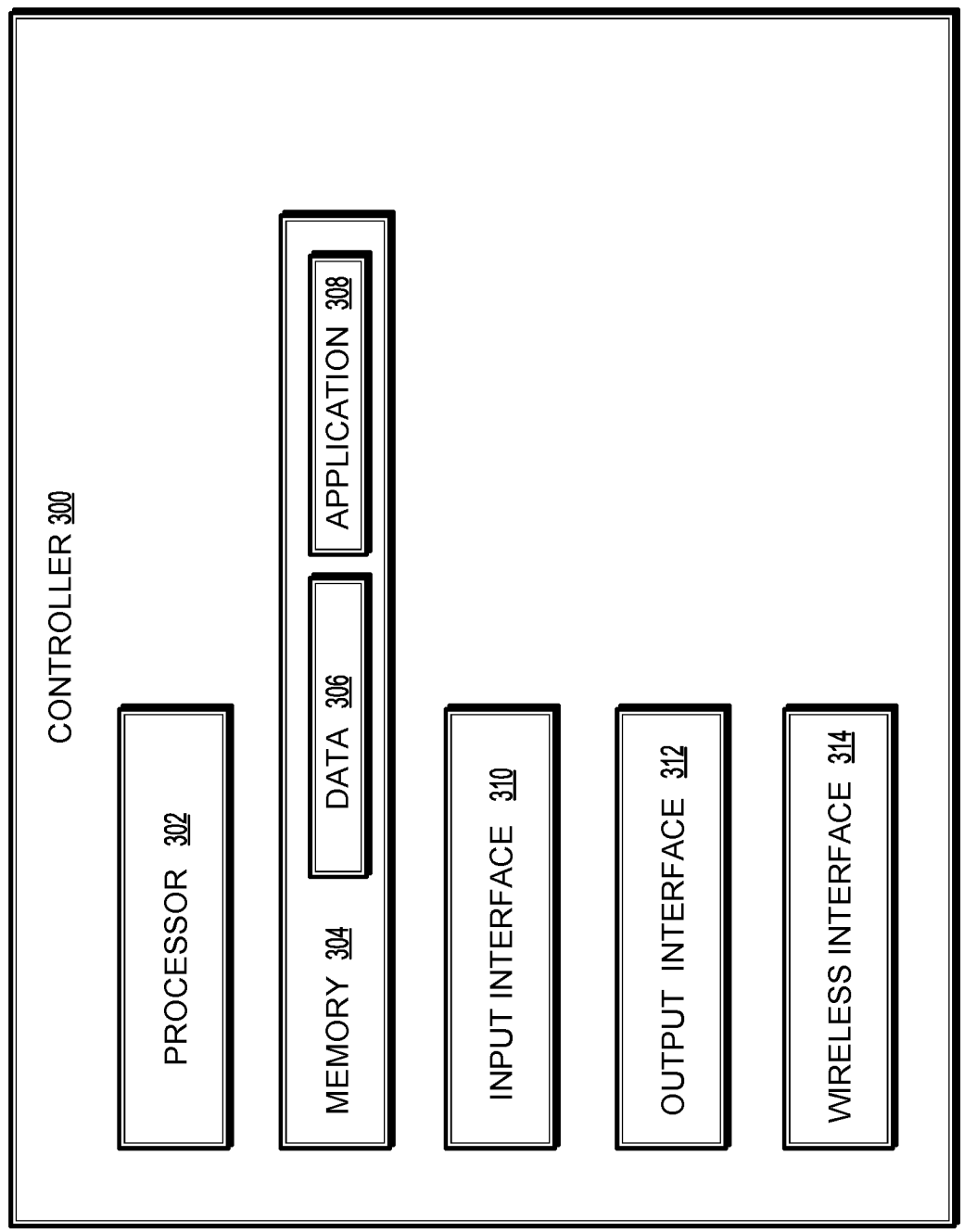
FIG. 12 is a schematic block diagram of a computing device that may be employed according to various embodiments of the present disclosure.

FIG. 12 illustrates a schematic diagram of a computing device that is configurable for operation of the tissue property sensing device 100 and designated generally as controller 300. Though not explicitly shown in figures of the present application, the controller 300, or one or more components thereof, may represent one or more components of the tissue property sensing device 100 (e.g., an input interface, output interface, or the like). In addition, the controller 300 may include one or more processors 302, memories 304, input interfaces 310, output interfaces 312, wireless interfaces 314, or any desired subset of components thereof.

The memory 304 includes non-transitory computer-readable storage media for storing data and/or software which include instructions that may be executed by the one or more processors 302. When executed, the instructions may cause the processor 302 to control operation of the controller 300, e.g., reception and transmission of sensor signals transmitted and received during operation of the one or more sensors "S" disposed along the head 148 of the piston 138 as well as the motor (not explicitly shown) associated with the first drive screw 208 (FIG. 11). More particularly, the controller 300 may receive the sensor signals, indicative of one or more light amplitude measurements, and store the sensor signals in the memory 304 of the controller 300. The sensor signals indicative of the light amplitude measurements may be stored with supplemental information including, but not limited to, time stamp information associated with the reception of the signals, device information associated with the device receiving the sensor signals (e.g., encoder measurements), and the like. In embodiments, the memory 304 includes non-transitory computer-readable storage media for storing data and/or software which includes instructions that may be executed by the one or more processors 302. The memory 304 may include one or more solid-state storage devices such as flash memory chips. Additionally, or alternatively, the memory 304 may include one or more mass storage devices in communication with the processor 302 through a mass storage controller and a communications bus (not shown). Although the description of computer readable media described in this disclosure refers to a solid-state storage device, it will be appreciated by one of ordinary skill that computer-readable media may include any available media that can be accessed by a processor 302. More particularly, computer readable storage media may include, without limitation, non-transitory, volatile, non-volatile, removable, non-removable media, and the like, implemented in any method of technology for storage of information such as computer readable instructions, data structures, program modules, or other suitable data access and management systems. Examples of computer-readable storage media include RAM, ROM, EPROM, EEPROM, flash memory, or other known solid state memory technology, CD-ROM, DVD, Blu-Ray, or other such optical storage, magnetic cassettes, magnetic tape, magnetic disk storage or other magnetic storage devices, or any other medium which may be used to store information and which can be accessed by the controller 300.

In embodiments, the memory 304 stores data 306 and/or one or more applications 308. Such applications 308 may include instructions which are executed on the one or more processors 302 of the controller 300. The applications 308 may include instructions which cause an input interface 310 and/or an output interface 312 to receive and transmit sensor signals, respectively, to and from the tissue property sensing device 100 and/or the handheld device 200. More particularly, as the at least one sensor "S" (see FIG. 1) senses one or more of the tissue properties discussed above, the at least one sensor "S" may, in response, transmit signals indicative of the measurements to the input interface 310. Once received by the input interface 310, the signals transmitted by the one or more sensors "S" may be stored in the at least one memory 304 of the controller 300. Additionally, or alternatively, the controller 300 may transmit the signals for analysis and/or display via the output interface 312. For example, the output interface 312 may transmit the sensor signals to a display device (not explicitly shown) either disposed on the tissue property sensing device 100, the handheld device 200, or a display located remotely relative to the tissue property sensing device 100. The memory 304 may further transmit and/or receive data via a wireless interface 314 via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE 802.15.4-2003 standard for wireless personal area networks (WPANs)). Although depicted as a separate component, the wireless interface 314 may be integrated into the input interface 310 and/or the output interface 312.

Figure 13A:
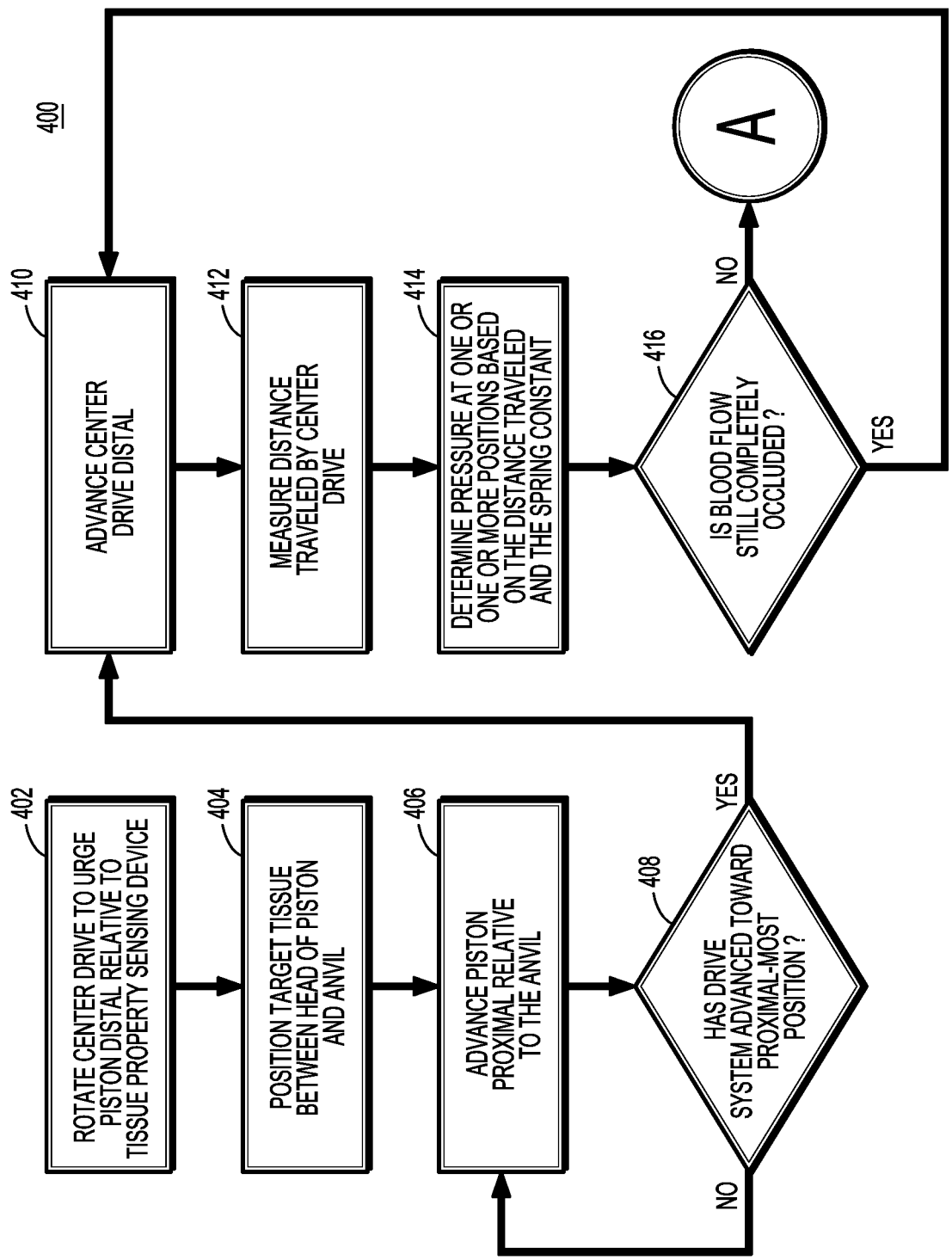
FIG. 13A illustrates a flow diagram of a process for controlling of the tissue property sensing device of FIG. 1, according to embodiments of the present disclosure.

Referring to FIG. 13A, a flow diagram associated with a method of measuring one or more tissue properties with a tissue property sensing device is illustrated and referred to generally as process 400.

Initially, the tissue property sensing device 100 is engaged by a clinician or by default instructions stored in the memory 304 to transition the tissue property sensing device 100 to an open configuration (block 402; see FIG. 5). This can take place prior to or after insertion of the tissue property sensing device 100 into a patient. To transition the tissue property sensing device 100 to the open configuration, the clinician may engage one or more input buttons (not explicitly labeled) on the handheld device 200. In response to the input, the controller 300 may receive and analyze the signal and, based on the analysis, cause the motor of the handheld device 200 to engage the one or more proximal connector sleeves 108 by rotating the one or more drive screws 208. Once the piston is advanced to a desired position (FIG. 5) (e.g., to the open configuration) the handheld device 200 stops the drive screw 208 from rotating further. It will be understood that, in embodiments, the memory 304 may cause the tissue property sensing device 100 to transition to the closed configuration prior to insertion of the distal portion of the tissue property sensing device 100 into the body of the patient. This may be done to collapse or otherwise prevent the piston from engaging or catching tissue during the insertion process, as well as for calibration of the tissue property sensing device 100 (e.g., to zero or otherwise initialize initial position measurements collected from the one or more encoders disposed about the tissue property sensing device 100).

Once the tissue property sensing device 100 is inserted into the patient, the target tissue "T" is positioned between the head 148 of the piston 138 and the head 152 of the anvil 150 (block 404). Next, the clinician engages the handheld device 200 to cause the sensing assembly to transition to an approximated configuration (see FIG. 7) (block 406). Specifically, the clinician engages one or more buttons on the handheld device 200 to cause the piston 138 to retract to a proximal-most position. As the piston 138 moves proximally, the controller 300 may receive sensor measurements from the one or more encoders to determine the position of the piston 138 relative to the center drive 124 (e.g., the components associated with the one or more encoders that remain stationary as the center drive 124, and by extension the piston 138, move proximally or distally). When the controller 300 determines that the piston 138 is not in a retracted position (block 408), the controller 300 continues to cause the piston 138 to move proximally to compress the tissue "T". Otherwise, once the controller 300 determines that the piston 138 is in a retracted position, the controller 300 prepares for a tissue property sensing phase. The retracted position may be any predetermined position or range of positions of the piston 138 and/or the center drive 124 relative to a fixed component of the tissue property sensing device (e.g., the inner shaft "IS" or outer shaft "OS") and may vary depending upon the thickness of the tissue "T".

Once in the retracted position (e.g., the closed configuration) the tissue "T" thickness may be determined. For example, a clinician may view the plurality of indicators 142 through the window 162 in the outer shaft "OS" and, based on the visible indicators, determine the thickness of the tissue between the head 148 of the piston 138 and the head 152 of the anvil 150. In embodiments, the controller 300 may determine the tissue thickness based on measurements received by the one or more encoders disposed about the tissue property sensing device 100. In addition to the tissue thickness, an initial pressure exerted by the sensing assembly onto the target tissue "T" may be determined. For example, based on sensor signals received indicating the position of the piston 138 relative to the center drive 124, a known spring constant of the tension spring 160, and the surface area of the head 148 of the piston 138 and the head 152 of the anvil 150, the controller 300 may determine the initial pressure exerted by the sensing assembly when the tissue property sensing device 100 is in the approximated configuration. It will be understood that the tension spring 160 may be selected such that, when in the approximated configuration, the sensing assembly applies a pressure known to occlude blood flow with the tissue "T". Confirmation of blood flow occlusion may be determined by the controller 300 based on one or more sensor measurements measured by the sensor "S" (e.g., one or more light amplitude measurements being within a predetermined range).

To determine a systolic blood pressure, the controller 300 may cause the motor of the handheld device 200 to rotate the one or more drive screws 208 to cause the center drive 124 to move distally toward the intermediate position until blood within the tissue begins to flow (block 410; see FIG. 9). Based on the measured distance which the piston 138 and/or the center drive 124 moved distal relative to one or more fixed components of the tissue property sensing device 100, the spring constant of the tension spring 160, and the surface area of the head 148 of the piston 138 and the head 152 of the anvil 150, the controller 300 determines the pressure exerted on the target tissue "T" by the sensing assembly (block 414) when blood within the tissue begins to flow again. Based upon this determination, blood pressure can be determined. If the controller 300 determines that the blood flow of the target tissue "T" is still completely occluded ("YES" at block 416) (e.g., no light amplitude measurements sensed by the sensor "S" exceed a predetermined measurement) the center drive 124 is moved distally (block 410) until blood begins to flow again in the tissue "T".

Similar to blocks 410-416, the tissue property sensing device 100 may move the center drive 124, and by extension the piston 138, to determine the diastolic pressure of the patient at the target tissue. To measure the diastolic blood pressure after the systolic blood pressure is measured, the controller 300 continues to cause the center drive 124 and the piston 138 to advance until blood flow is fully restored within the tissue "T" (block 420). When this occurs, the pressure exerted on the target tissue "T" may be determined as described above. This pressure corresponds to the diastolic blood pressure of the patient taken at the target tissue (e.g., the light amplitude measurements may consistently be greater than a predetermined light amplitude measurement threshold, indicating that blood flow has completely returned to the target tissue (block 428)).

Once the desired blood pressure is determined (systolic, diastolic, or both) the controller 300 may transition the tissue property sensing device 100 toward the open configuration. This may be achieved by engaging the motor of the handheld device 200 to rotate the one or more drive screws 208 and advance the center drive 124 to a proximal-most position (e.g., the open configuration). Once the tissue is removed from the sensing assembly, the tissue property sensing device 100 may be positioned about target tissue, with process 400 repeated to determine the systolic and/or diastolic pressure at that target tissue.

In embodiments, where removal of the inserted portion of the tissue property sensing device 100 from the patient is desired, the tissue property sensing device 100 may be transitioned to the approximated configuration for removal. To do so, the controller 300 may cause the motor of the handheld device 200 to rotatably engage the proximal connector sleeve 108, thereby causing the center drive to move proximally. Specifically, the controller 300 may receive manual input from the clinician (e.g., by determining one or more input buttons are engaged) and in response engage the motor. Once the head 148 of the piston 138 is flush with the head 152 of the anvil 150, the tissue property sensing device 100 may be removed from the patient.

It will be understood that various modifications may be made to the embodiments disclosed herein. In embodiments, the sensors may be disposed on any suitable portion of the robotic arm. Therefore, the above description should not be construed as limiting, but merely as exemplifications of various embodiments. Those skilled in the art will envision other modifications within the scope and spirit of the claims appended thereto.

What is claimed is:

1. A tissue property sensing system, comprising:
    an adapter assembly including a drive interface;
    a drive screw coupled to the drive interface and extending from the adapter assembly; and
    a sensing assembly including:
        an outer shaft;
        an anvil supported on a distal portion of the outer shaft;
        a center drive movable within the outer shaft and defining a longitudinal bore configured to receive the drive screw;
        a piston movable within the outer shaft and including a distal arm having a distal portion, and a head extending from the distal portion of the distal arm, the piston being movable within the outer shaft to move the head in relation to the anvil between an open configuration and a closed configuration, wherein in the closed configuration, the head of the piston and the anvil are positioned to clamp and occlude blood flow in tissue;
        a sensor supported on the head of the piston; and
        a tension spring coupled to the center drive and to the piston to urge the piston towards the center drive and to urge the head of the piston towards the anvil.

2. The tissue property sensing system according to claim 1, wherein the piston includes a proximal arm and the center drive includes a housing, the proximal arm being received within the housing to prevent rotational movement of the piston in relation to the center drive.

3. The tissue property sensing system according to claim 2, wherein the outer shaft defines a window, and the proximal arm of the piston supports a plurality of indicators, one or more of the plurality of indicators being visible through the window in the closed configuration to indicate a thickness of tissue positioned between the head of the piston and the anvil.

4. The tissue property sensing system according to claim 1, wherein the center drive includes a threaded opening, and a portion of the drive screw is received within the threaded opening such that rotation of the drive screw in relation to the center drive causes longitudinal movement of the center drive within the outer shaft.

5. The tissue property sensing system according to claim 4, wherein rotation of the drive screw in a first direction causes the center drive to advance distally in relation to the adapter assembly and rotation of the drive screw in a second direction causes the center drive to advance proximally in relation to the adapter assembly.

6. The tissue property sensing system according to claim 2, wherein in the closed configuration, the sensing assembly applies a predetermined range of forces to tissue disposed within the sensing assembly.

7. The tissue property sensing system according to claim 1, wherein the center drive supports a fixation pin that is disposed within the longitudinal bore, the tension spring being coupled to the fixation pin.

8. A sensing assembly comprising:
    an outer shaft;
    an anvil supported on a distal portion of the outer shaft;
    a center drive movable within the outer shaft and defining a longitudinal bore, the center drive having a base defining a threaded bore that is configured to receive a drive screw;
    a piston movable within the outer shaft and including a distal arm having a distal portion, and a head extending from the distal portion of the distal arm, the piston movable within the outer shaft to move the head in relation to the anvil between an open configuration and a closed configuration, wherein in the closed configuration, the head of the piston and the anvil are positioned to clamp tissue to occlude blood flow in the tissue;
    a sensor supported on the head of the piston; and a tension spring coupled to the center drive and to the piston to urge the piston towards the center drive and to urge the head of the piston towards the anvil.

9. The sensing assembly according to claim 8, wherein the piston includes a proximal arm and the center drive includes a housing, the proximal arm received within the housing to prevent rotational movement of the piston in relation to the center drive.

10. The sensing assembly according to claim 9, wherein in the closed configuration, the sensing assembly applies a predetermined range of forces to tissue disposed within the sensing assembly.

11. The sensing assembly according to claim 9, wherein the outer shaft defines a window and the proximal arm of the piston supports a plurality of indicators, one or more of the plurality of indicators being visible through the window in the closed configuration to indicate a thickness of tissue positioned between the head of the piston and the anvil.

12. The sensing assembly according to claim 8, wherein the center drive supports a fixation pin that is disposed within the longitudinal bore, the tension spring coupled to the fixation pin.

13. The sensing assembly according to claim 12, wherein the fixation pin extends across the longitudinal bore of the center drive.

14. A system for occluding blood flow in tissue, the system comprising:
   an adapter assembly including a drive interface;
   a drive screw extending from the adapter assembly and coupled to the drive interface; and
   an assembly including:
      an outer shaft;
      an anvil supported on a distal portion of the outer shaft;
      a drive member movable within the outer shaft and defining a bore configured to receive the drive screw;
      a piston movable within the outer shaft and including an arm having a distal portion supporting a head, the piston movable within the outer shaft to move the head in relation to the anvil between an open configuration and a closed configuration, wherein in the closed configuration, the head of the piston and the anvil are positioned to clamp and occlude blood flow in tissue; and
      a spring coupled to the drive member and to the piston to urge the piston towards the drive member and to urge the head of the piston towards the anvil.

15. The system according to claim 14, wherein the outer shaft defines a window, and the piston supports a plurality of indicators, one or more of the plurality of indicators being visible through the window in the closed configuration to indicate a thickness of tissue positioned between the head of the piston and the anvil.

16. The system according to claim 14, further including a sensor disposed on one of the head of the piston and the anvil.

17. The system according to claim 14, wherein the drive member supports a fixation pin that is disposed within the bore of the drive member, the spring being coupled to the fixation pin.

* * * * *